United States Patent [19]

Meislin

[11] Patent Number: 6,039,753

[45] Date of Patent: Mar. 21, 2000

[54] SINGLE UNIT SURGICAL FASTENER AND METHOD

[76] Inventor: Robert Meislin, 6234 N. 47 St., Paradise Valley, Ariz. 85253

[21] Appl. No.: 09/116,512

[22] Filed: Jul. 16, 1998

[51] Int. Cl.[7] .................................................. A61B 17/00
[52] U.S. Cl. ............................. 606/213; 606/72; 606/139
[58] Field of Search .................................... 606/139, 213, 606/215, 219, 220, 151, 144, 72, 73

[56] References Cited

U.S. PATENT DOCUMENTS 4,532,926  8/1985  O'Holla ................................. 606/220
4,976,715  12/1990  Bays et al. ................................. 606/77

*Primary Examiner*—Michael Buiz
*Assistant Examiner*—Vikki Trinh
*Attorney, Agent, or Firm*—Harry M. Weiss; Jeffrey Weiss; Paul W. Davis

[57] ABSTRACT

A single unit surgical fastener and system and method for repairing torn meniscus tissue in an arthroscopic, all-inside procedure. The desired length of the single unit surgical fastener is first determined by measuring the distance from the interior of the meniscus across the tear and across the joint capsule, and then a single unit surgical fastener of desired length is then inserted across the tear in one or more places through a curved, slotted cannula.

30 Claims, 2 Drawing Sheets

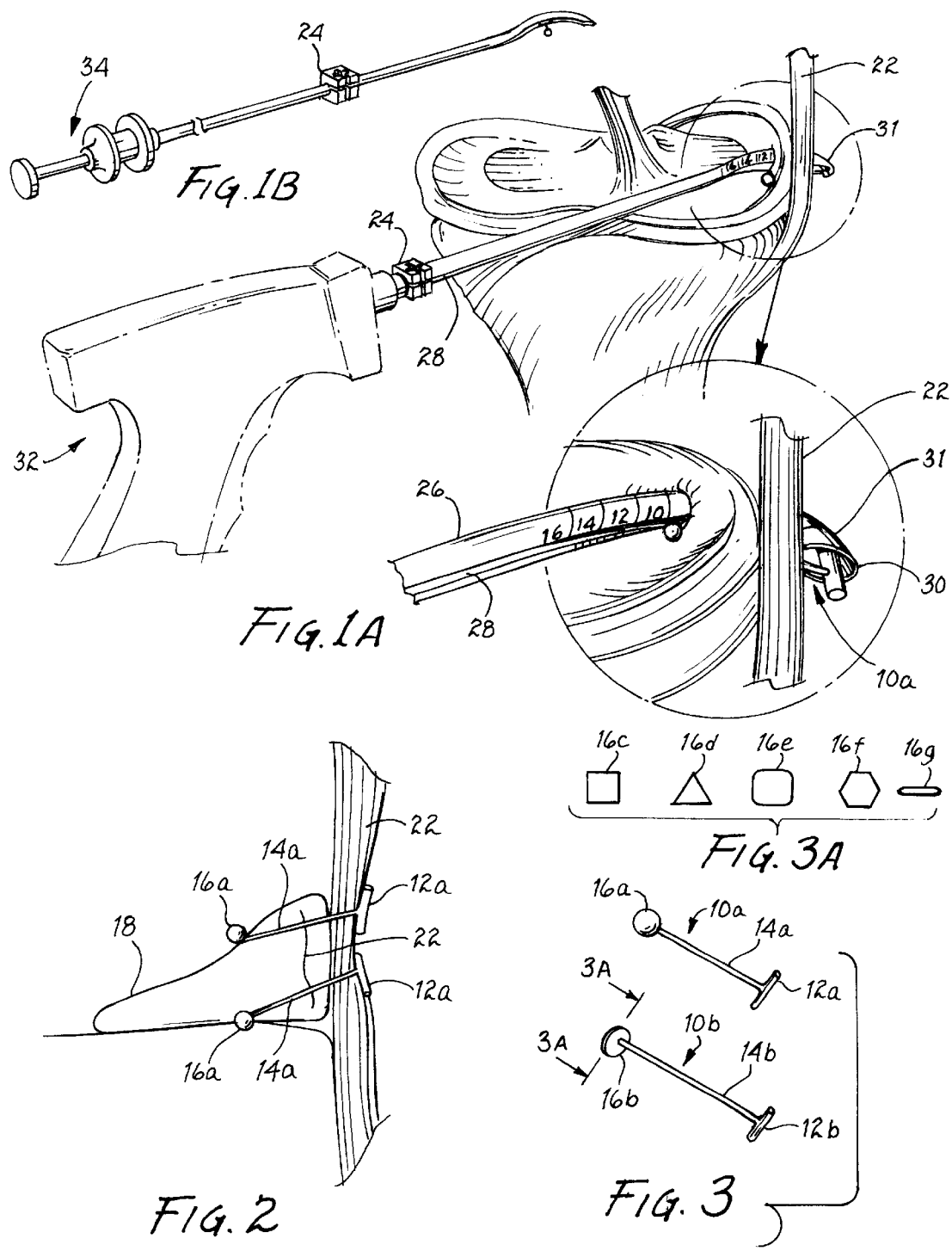

SINGLE UNIT SURGICAL FASTENER AND METHOD

BACKGROUND OF THE INVENTION

1. Field of the Invention

This invention relates to surgical sutures and suturing systems generally and, more particularly, to a single unit surgical fastener and system for repairing torn meniscus tissue and method therefor.

2. Description of the Prior Art

There are a number of different sutures and fasteners in use for repairing torn meniscus tissue, as well as a number of different systems for using such sutures and fasteners. The types of sutures and fasteners currently in use include ordinary surgical sutures, barbs, staples, H-shaped fasteners, and combination suture/fasteners.

Since the advent of arthroscopic surgical technology, sutures have been used in one or more of the four techniques that are currently in general clinical use: (a) open meniscal repair—involving exposure of the capsule through a longitudinal incision, preparation of the meniscal rim and capsula bed, and placement of vertically and/or horizontally oriented sutures across the tear; (b) arthroscopic inside-out repair—involving a small posterior incision carried down to the capsule for suture retrieval, the placement of sutures inside the knee arthroscopically, and the tying of sutures over the capsule; (c) arthroscopic outside-in repair—involving incisions made perpendicular to the joint line, the placement of a spinal needle across the tear from outside to inside the knee, the passing of sutures through the needle and into the joint, and the tying of the suture with multiple knots outside the knee followed by the pulling of these knotted sutures into the knee joint and the tying of the sutures outside the knee joint; and (d) arthroscopic all-inside repair—involving the piercing of both sides of the tear with a cannulated suture hook, the passing of the suture through the hook and across the tear, and the securing of the sutures using a knot pusher.

The indications for the four surgical techniques, and the relative risks and benefits of each, are varied. However, where possible, the all-inside technique is generally considered the most advantageous because it avoids the necessity for additional incisions beyond the initial incision and limits risk to the neurovascular bundle located in the posterior aspect of the knee.

Over the years, a number of fasteners have been developed to be used as alternatives to sutures. For example, U.S. Pat. No. 5,320,633 shows an H-shaped fastener that is delivered using a straight cannula, which cannula is guided into the meniscus using a guide pin. U.S. Pat. No. 4,873,976 shows an arrow-type surgical fastener for use in repairing meniscus tissue. U.S. Pat. No. 4,635,637 shows a twin-barbed fastener for use in repairing meniscus tissue. U.S. Pat. No. 5,562,704 shows a surgical implant having a plurality of cuts in the body to arrest the implant in position. There are relative advantages and disadvantages to these fasteners; however, none of these references shows a delivery system using a cannula that has been curved to conform to the concavity and convexity of the knee and to thus reduce the risk of injury to the neurovascular bundle in the posterior aspect of the knee. Moreover, these references do not disclose a method for effectively compressing the tear in the meniscus for purposes of accurately measuring the size of fastener needed—using the same cannula that is used to deliver the fastener and thus avoiding the need for additional incisions or insertions. The lack of an effective measuring system can lead to the obviously undesirable result of using a fastener of improper size in meniscus repair.

Hybrid suture/fasteners have also been developed as an alternative to simple sutures. U.S. Pat. Nos. 4,741,330 and 5,269,809 are examples of two such hybrid designs. However, the need to cut and tie off the sutures and to otherwise secure the suture/fastener in place makes these devices more complicated to use than single unit fasteners, and extends the amount of time required for the surgical repair of the meniscus.

Therefore, a need existed for a meniscus repair device and system allowing for relatively quick repair of torn meniscus tissue, with a minimum of incisions and thus preferably usable in an all-inside procedure. The improved device and system must also provide for accurate measurement of the desired fastener length—using the same instrument used to insert and position the fastener and without the need for an additional incision or the insertion into the knee of a second instrument. Finally, the improved device and system must reduce the risk of injury to the neurovascular bundle located in the posterior aspect of the knee. The single unit surgical fastener and system and method of the present invention provides these and other related advantages.

SUMMARY OF THE INVENTION

It is an object of this invention to provide an improved single unit fastener and system for the repair of torn meniscus tissue and method therefor.

It is a further object of this invention to provide an improved single unit fastener and system for use in an all-inside meniscus repair procedure.

It is a further object of this invention to provide an improved single unit fastener and system having a curved cannula to reduce the risk of injury to the neurovascular bundle in the posterior aspect of the knee.

It is a further object of this invention to provide an improved single unit fastener and system allowing for precise measurement of the desired length of fastener to be used.

BRIEF DESCRIPTION OF THE PREFERRED EMBODIMENTS

In accordance with one embodiment of the present invention, a system for repairing torn meniscus tissue is disclosed. It comprises, in combination: a single unit surgical fastener comprising: a substantially rod-shaped base member; a substantially rod-shaped shaft extending from the substantially rod-shaped member; and a retaining member at an end of the substantially rod-shaped shaft; means for positioning and inserting the single unit surgical fastener into the torn meniscus tissue comprising: a slotted cannula having a sharpened tip; the slotted cannula being dimensioned to receive the substantially rod-shaped base member of the single unit surgical fastener; the sharpened tip of the slotted cannula further being curved to conform to the shape of a knee; and insertion means dimensioned to fit within the slotted cannula for inserting the single unit surgical fastener through the torn meniscus tissue.

In accordance with a further embodiment of the present invention, a method for repairing torn meniscus tissue is disclosed. The method comprises the steps of: providing a single unit surgical fastener comprising: a substantially rod-shaped base member; a substantially rod-shaped shaft extending from the substantially rod-shaped member; and a retaining member at an end of the substantially rod-shaped shaft; providing means for positioning and inserting the single unit surgical fastener into the torn meniscus tissue comprising: a slotted cannula having a sharpened tip; the slotted cannula being dimensioned to receive the substantially rod-shaped base member of the single unit surgical fastener; the sharpened tip of the slotted cannula further being curved to conform to the shape of a knee; and insertion means dimensioned to fit within the slotted cannula for inserting the single unit surgical fastener into the torn meniscus tissue; making an incision in an anterior portion of the knee area for permitting access to an inside portion of a torn meniscus; inserting into the incision the slotted cannula; entering the inside portion of the torn meniscus with the slotted cannula and penetrating through the tear in the torn meniscus and through a proximal joint capsule; inserting the substantially rod-shaped base member of the single unit surgical fastener into the slotted cannula until the substantially rod-shaped base member passes through the tear in the meniscus and through the proximal joint capsule; releasing the single unit surgical fastener from the slotted cannula; and withdrawing the slotted cannula from the incision.

BRIEF DESCRIPTION OF THE DRAWINGS

FIG. 1A is a perspective view of a single unit surgical fastener of the present invention being inserted into a meniscus in an all-inside procedure using a curved, trigger-operated cannula, including a magnified view of the attachment point showing measuring gradations on the exterior of the cannula.

FIG. 1B is a perspective view of a plunger-type curved cannula of the present invention.

FIG. 2 is a side view of a torn meniscus tissue following repair using two single unit surgical fasteners of the present invention wherein each fastener has a spherical retaining member.

FIG. 3 is a perspective view of two embodiments of the single unit surgical fastener of the present invention, one having a spherical retaining member and the other having a disk-shaped retaining member.

FIG. 3A is a top view showing alternative embodiments of the retaining member of the single unit surgical fastener of the present invention.

DESCRIPTION OF THE PREFERRED EMBODIMENTS

Figure 4:
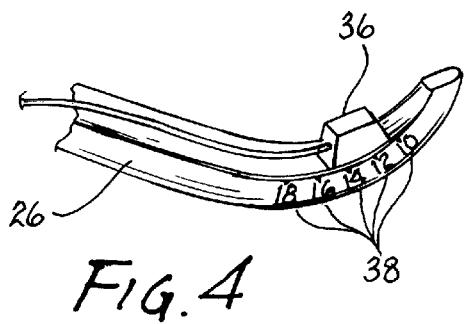
FIG. 4 is a side view of the curved tip portion of the curved cannula of the present invention, showing the tear compression/fastener measuring system.

Referring to FIG. 3, reference numbers 10a and 10b refer to two embodiments of the single unit surgical fastener of the present invention. The single unit surgical fastener 10a comprises a substantially rod-shaped base member 12a, a substantially rod-shaped shaft 14a extending from the base member 12a, and a spherical retaining member 16a. The single unit surgical fastener 10b comprises a substantially rod-shaped base member 12b, a substantially rod-shaped shaft 14b extending from the base member 12b, and a disk-shaped retaining member 16b. Referring to FIG. 3A, five different embodiments of a retaining member are shown, including a rectangular retaining member 16c, a triangular retaining member 16d, a substantially rectangular retaining member 16e having rounded corners, a six-sided retaining member 16f, and a substantially rod-shaped member 16g having substantially the same configuration as the base member 12a.

Figure 5:
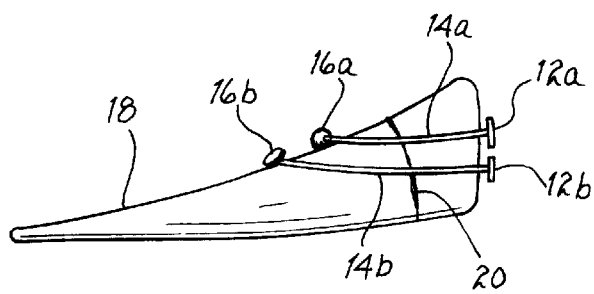
FIG. 5 is a side view of a torn meniscus tissue following repair using two single unit surgical fasteners of the present invention wherein one fastener has a spherical retaining member and one fastener has a disk-shaped retaining member.

Referring now to FIGS. 2 and 5, single unit fasteners 10a and 10b (shown in FIG. 5 only) are shown in position through a meniscus 18 having a tear 20. Referring specifically to FIG. 2, the preferred placement of the base member 12a of the single unit fastener 10a is shown, outside the joint capsule 22.

Figure 7:
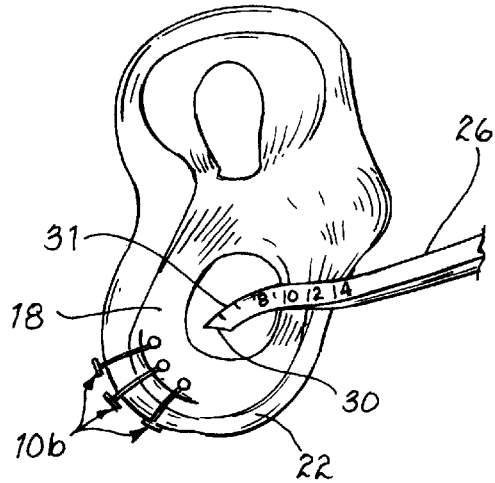
FIG. 7 is a top view of a meniscus that has been repaired with three single unit surgical fasteners of the present invention in an all-inside procedure.

Referring now to FIGS. 1A and 7, the insertion of a single unit fastener 10a (FIG. 1A) and 10b (FIG. 7) is shown. Referring specifically to FIG. 1A, and using the single unit fastener 10a as an example, the base member 12a is inserted into a receiver 24 located on a slotted cannula 26, until the base member 12a is within the slotted cannula 26 and the shaft 14a is extending through the slot 28 in the slotted cannula 26. The rim of the open end 30 of the slotted cannula 26 is sharpened, so as to permit ready penetration of the meniscus 18 and joint capsule 22. The end portion 31 of the slotted cannula 26 is curved to conform to the natural convexity and concavity of the knee, so as to reduce the risk of unintended penetration into the neurovascular bundle in the posterior aspect of the knee. The open end 30 is inserted from the interior of the joint through the meniscus 18, through the tear 20, and then through the joint capsule 22—which insertion is guided by the surgeon using an arthroscope (not shown)—until the base member 12a is on the other side of the joint capsule 22. The actual insertion of the single unit fastener 10a is actuated using a trigger-actuated mechanism 32 or a plunger actuated mechanism 34 (see FIG. 1B). Other types of insertion mechanism may also be used without departing from the spirit or scope of the invention.

Figure 6:
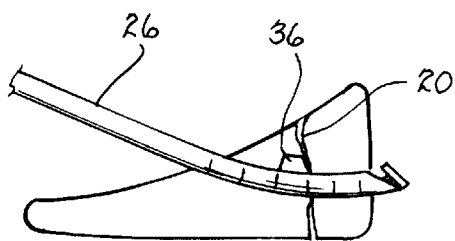
FIG. 6 is a side view of the curved tip portion of the curved cannula of the present invention, showing the operation of the tear compression/fastener measuring system.

Referring now to FIGS. 4 and 6, a measuring system for use with the slotted cannula 26 is demonstrated. Located within the slotted cannula 26 is a compression member 36, which may be inserted in the direction of the tear 20 using the same actuation systems discussed above. The compression member 36 travels within the slot 18 in the slotted cannula 26, and extends partially out of the slot 18 so as to be viewable in relation to a series of numbered gradations 38 located on a side of the slotted cannula 26 proximate the open end 30. The gradations 38 measure, preferably in millimeters and preferably in two millimeter increments, the distance from the open end 30. As shown more specifically in FIG. 6, the compression member 36 is inserted until it compresses the open ends of the tear 20 against each other. Then, using an arthroscope (not shown), the location of the portion of the compression member 36 proximate the tear 20 is noted relative to the gradations 38—thus recording the desired length of a single unit fastener 10a to be used to repair the tear 20. The compression member 36 is then removed from the slotted cannula 26, and a single unit fastener 10a is selected that conforms to the measurement arrived at with the use of the compression member 36. The single unit fastener 10a is then inserted as described above. The entire process may be repeated at a plurality of locations, as shown for example in FIGS. 2, 5, and 7.

Figure 8:
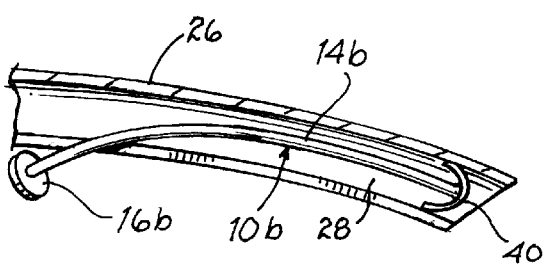
FIG. 8 is a partially cross-sectional side view of the slotted cannula showing an alternative embodiment of the base member of the single unit surgical fastener of the present invention.

Referring to FIG. 8, an alternative embodiment of the single unit fastener 10b is shown. In this embodiment, the single unit fastener 10b has the retaining member 16b and the substantially rod-shaped shaft 14b extending through the slot 28 as described above. However, instead of the substantially rod-shaped base member 12b, in this embodiment the single unit fastener 10b has a base member 40 which can be any one of the retaining members 16c–16f described above, wherein the base member 40 is folded preferably as shown in FIG. 8 to fit within the receiver 24 and thus into the barrel of the slotted cannula 26. Upon release from the slotted cannula 26 and insertion outside the capsule 22 as described above, the base member 40 will unfold—thus reverting to its original configuration and providing more resistance to being pulled back through the capsule 22 than a base member having less surface area.

While the invention has been particularly shown and described with reference to preferred embodiments thereof, it will be understood by those skilled in the art that the foregoing and other changes in form and details may be made therein without departing from the spirit and scope of the invention.

What is claimed is:

1. A system for repairing torn meniscus tissue comprising, in combination:
    a single unit surgical fastener comprising:
        a base member;
        a substantially rod-shaped shaft extending from said substantially rod-shaped member; and
        a retaining member at an end of said substantially rod-shaped shaft;
    means for positioning and inserting said single unit surgical fastener into said torn meniscus tissue comprising:
        a slotted cannula having a first section having an axial bore and a second section continuous with said first section and curved so as to conform to the shape of a knee and to extend laterally from an axis established by said axial bore;
        a sharpened tip located at a distal end of said second section;
        said slotted cannula being dimensioned to receive said base member of said single unit surgical fastener; and
        insertion means dimensioned to fit within said slotted cannula for inserting said single unit surgical fastener through said torn meniscus tissue.

2. The system of claim 1 wherein said retaining member is substantially spherical.

3. The system of claim 1 wherein said retaining member is substantially disk-shaped.

4. The system of claim 1 wherein said retaining member is substantially rectangular.

5. The system of claim 1 wherein said retaining member is substantially triangular.

6. The system of claim 1 wherein said retaining member has more than four sides.

7. The system of claim 1 wherein said retaining member is substantially rod-shaped.

8. The system of claim 1 wherein said base member is substantially disk-shaped.

9. The system of claim 1 wherein said base member is substantially rectangular.

10. The system of claim 1 wherein said base member is substantially triangular.

11. The system of claim 1 wherein said base member has more than four sides.

12. A system for repairing torn meniscus tissue comprising in combination:
    a single unit surgical fastener comprising:
        a base member;
        a substantially rod-shared shaft extending from said substantially rod-shaped member; and
        a retaining member at an end of said substantially rod-shaped shaft;
    means for positioning and inserting said single unit surgical fastener into said torn meniscus tissue comprising:
        a slotted cannula having a sharpened tip;
        said slotted cannula being dimensioned to receive said base member of said single unit surgical fastener;
            wherein said slotted cannula further comprises a plurality of gradations viewable with an arthroscope wherein said gradations are located on an exterior portion of said cannula proximate said sharpened tip and wherein said gradations measure distance from said sharpened tip;
        said sharpened tin of said slotted cannula further being curved to conform to the shape of a knee; and
        insertion means dimensioned to fit within said slotted cannula for inserting said single unit surgical fastener through said torn meniscus tissue.

13. The system of claim 12 wherein said plurality of gradations are spaced approximately two millimeters from one another.

14. The system of claim 12 wherein said means for positioning and inserting said single unit surgical fastener further comprises:
    compression means for compressing a tear in meniscus tissue in the direction of a proximal joint capsule;
    said compression means comprising a member inserted into said slotted cannula;
    said compression means further being visible relative to said plurality of gradations with an arthroscope.

15. A system for repairing torn meniscus tissue comprising in combination:
    a single unit surgical fastener comprising:
        a base member;
        a substantially rod-shaped shaft extending from said substantially rod-shaped member; and
        a retaining member at an end of said substantially rod-shaped shaft;
    means for positioning and inserting said single unit surgical fastener into said torn meniscus tissue comprising:
        a slotted cannula having a sharpened tip;
        said slotted cannula being dimensioned to receive said base member of said single unit surgical fastener;
        said sharpened tip of said slotted cannula further being curved to conform to the shape of a knee;
        insertion means dimensioned to fit within said slotted cannula for inserting said single unit surgical fastener through said torn meniscus tissue; and
        compression means for compressing a tear in meniscus tissue in the direction of a proximal joint capsule;
        said compression means comprising a member inserted into said slotted cannula;
        said compression means further being visible with an arthroscope.

16. A method for repairing torn meniscus tissue comprising the steps of:
    providing a single unit surgical fastener comprising:
        a base member;

a substantially rod-shaped shaft extending from said substantially rod-shaped member; and a retaining member at an end of said substantially rod-shaped shaft;

providing means for positioning and inserting said single unit surgical fastener into said torn meniscus tissue comprising:

a slotted cannula having a sharpened tip;

said slotted cannula being dimensioned to receive said base member of said single unit surgical fastener;

said sharpened tip of said slotted cannula further being curved to conform to the shape of a knee; and insertion means dimensioned to fit within said slotted cannula for inserting said single unit surgical fastener into said torn meniscus tissue;

making an incision in an anterior portion of the knee area for permitting access to an inside portion of a torn meniscus;

inserting into said incision said slotted cannula;

entering said inside portion of said torn meniscus with said slotted cannula and penetrating through said tear in said torn meniscus and through a proximal joint capsule;

inserting said substantially rod-shaped base member of said single unit surgical fastener into said slotted cannula until said substantially rod-shaped base member passes through said tear in said meniscus and through said proximal joint capsule;

releasing said single unit surgical fastener from said slotted cannula; and withdrawing said slotted cannula from said incision.

17. The method of claim 16 wherein said retaining member is substantially spherical.

18. The method of claim 16 wherein said retaining member is substantially disk-shaped.

19. The method of claim 16 wherein said retaining member is substantially rectangular.

20. The method of claim 16 wherein said retaining member is substantially triangular.

21. The method of claim 16 wherein said retaining member has more than four sides.

22. The method of claim 16 wherein said retaining member is substantially rod-shaped.

23. The method of claim 16 wherein said base member is substantially disk-shaped.

24. The method of claim 16 wherein said base member is substantially rectangular.

25. The method of claim 16 wherein said base member is substantially triangular.

26. The method of claim 16 wherein said base member has more than four sides.

27. The method of claim 16 wherein said base member is substantially rod-shaped.

28. The method of claim 16 wherein said step of providing said slotted cannula further comprises the step of providing a plurality of gradations viewable with an arthroscope wherein said gradations are located on an exterior portion of said cannula proximate said sharpened tip and wherein said gradations measure distance from said sharpened tip.

29. The method of claim 28 wherein said plurality of gradations are spaced approximately two millimeters from one another.

30. The method of claim 28 further comprising the steps of:

providing compression means for compressing a tear in meniscus tissue in the direction of a proximal joint capsule;

said compression means comprising a member inserted into said slotted cannula;

said compression means further being visible relative to said plurality of gradations with an arthroscope.

* * * * *